United States Patent [19]
Dahl et al.

[11] Patent Number: 5,554,178
[45] Date of Patent: Sep. 10, 1996

[54] METALIZED IMPLANTABLE CARDIAC ELECTRODE

[75] Inventors: Roger W. Dahl, Andover, Minn.; David Lipson, Indianapolis, Ind.

[73] Assignee: Cardiac Pacemakers, Inc., St. Paul, Minn.

[21] Appl. No.: 427,942

[22] Filed: Apr. 26, 1995

Related U.S. Application Data

[63] Continuation of Ser. No. 24,176, Feb. 22, 1993, abandoned.
[51] Int. Cl.$^6$ ............................................. A61N 1/05
[52] U.S. Cl. ............................................. 607/122
[58] Field of Search ........................... 607/119, 121–132, 607/152; 128/642

[56] References Cited

U.S. PATENT DOCUMENTS

| | | | |
|---|---|---|---|
| 3,804,098 | 4/1974 | Friedman | 128/404 |
| 4,224,949 | 9/1980 | Scott et al. | 128/642 |
| 5,016,646 | 5/1991 | Gotthardt et al. | 607/119 |
| 5,109,842 | 5/1992 | Adinolfi | 128/642 |
| 5,199,433 | 4/1993 | Metzger et al. | 607/124 |
| 5,238,006 | 8/1993 | Markowitz | 128/642 |
| 5,269,810 | 12/1993 | Hull et al. | 128/642 |
| 5,282,468 | 2/1994 | Klepinski | 128/642 |

FOREIGN PATENT DOCUMENTS

| | | | |
|---|---|---|---|
| 2822829 | 11/1979 | Germany | 607/122 |
| 2107229 | 4/1990 | Japan | 128/642 |
| 4044775 | 2/1992 | Japan | 607/129 |

OTHER PUBLICATIONS

Pochay et al., "A Multichannel Depth Probe Fabricated Using Electron–Beam Lithography," IEEE Transactions of Biomedial Engineering, vol. BME–26, No. 4, Apr. 1979, pp. 199–206.

*Primary Examiner*—William E. Kamm
*Attorney, Agent, or Firm*—Schwegman, Lundberg, Woessner & Kluth, P.A.

[57] ABSTRACT

An implantable cardiac electrode includes a flexible polymeric substrate, a metallized surface layer of the polymeric substrate forming one or more electrically conductive regions on the surface of the polymeric substrate, and one or more insulated conductors connecting the electrically conductive regions to leads, the leads being connected to a cardiac monitoring and pulse generating system. In one embodiment, the electrically conductive region forms a band on the outer surface of a polymeric tube and is electrically connected to a conductor embedded in the tube. In another embodiment, the electrically conductive region forms a desired configuration on a planar surface of the polymeric substrate, such as a concentric ring or spiral patch configuration. In these and other embodiments, the metallized surface layer includes a surface layer of the polymeric substrate that is impregnated with a metal such that a conductive region is formed in the surface of the otherwise insulative polymeric substrate.

5 Claims, 6 Drawing Sheets

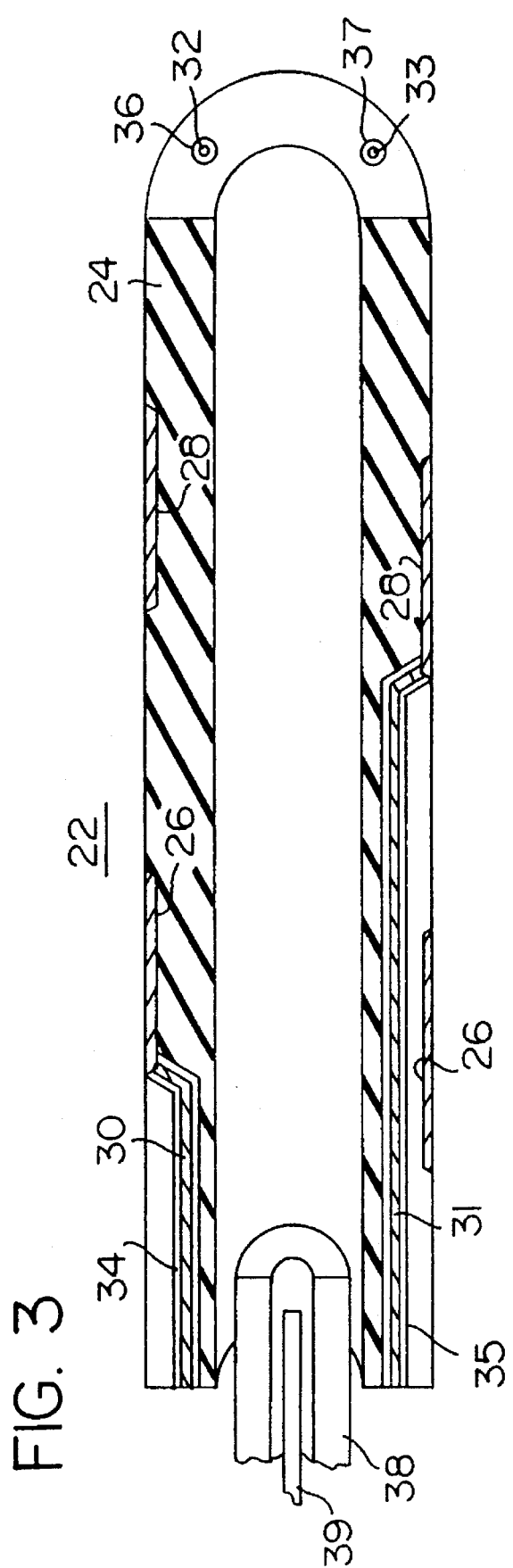

METALIZED IMPLANTABLE CARDIAC ELECTRODE

CROSS REFERENCE TO RELATED APPLICATION

This application is a continuation of application Ser. No. 08/024,176, filed Feb. 22, 1993, now abandoned.

BACKGROUND OF THE INVENTION

This invention relates generally to an electrode, and more particularly to a biologically compatible implantable electrode for applications such as a cardiac pacemaking or cardioversion, including heart stimulation and monitoring.

Electrodes implanted in the body for electrical cardioversion or pacing of the heart are well known. More specifically, electrodes implanted in or about the heart have been used to reverse (i.e., defibrillate or cardiovert) certain life threatening arrhythmias, or to stimulate contraction (pacing) of the heart, where electrical energy is applied to the heart via the electrodes to return the heart to normal rhythm. See, for example, commonly assigned U.S. Pat. No. 5,063,932 to Dahl et al., relating to defibrillation discharge electrode configurations and particularly to fixed planar discharged configurations, and U.S. Pat. No. 4,559,951 to Dahl et al., relating to intravascular tubular electrodes, both of which are incorporated herein by reference.

U.S. Pat. No. 5,063,932 specifically discloses an implantable cardiac electrode comprised of a planar conductive material, typically imbedded in an insulated material. Various geometric configurations of the conductive material are disclosed, taking advantage of the "edge effect" to more efficiently discharge energy.

U.S. Pat. No. 4,559,951 discloses a flexible tubular catheter assembly in which conductive coils are imbedded in the walls of the tube and connected to conductive surfaces (i.e., surface electrodes) on the tip of the catheter assembly or on the tubular surface. A catheter assembly is thus provided which allows for the use of a plurality of separate electrode surfaces without necessitating the increase in overall diameter of the catheter as additional groups of conductor coils are added.

Historically, implantable electrodes have been constructed using discrete metal parts such as rings, helically wound coils, or screens. As pacer and cardioverting devices have become more sophisticated, the electrodes therewith have also increased in complexity, and often in overall size. With each sensor system requiring a dedicated electrode, a set of electrically isolated conductors is necessary to insure sensor isolation. Where these electrodes and leads are threaded through the body's vascular system, it is important that the overall diameter of the lead and its stiffness be minimized. Also, in order to minimize trauma to the tissue adjacent to the electrode, it is desirable to reduce the surface roughness and motion at the electrode-tissue interface.

A more recent system, as disclosed in U.S. Pat. No. 4,972,846 to W. L. Gore, utilizes a laminated structure where a plated metal coating is located between two porous polymeric materials to form a patch or planar electrode. However, the use of a metal plated coating leaves the metal discharge layer subject to high localized stresses when the electrode is flexed, which in turn can cause polymeric and metallic fatigue problems. Further, the overall resistance, as well as changes in resistance level during flexing, disclosed in the Gore patent are undesirably high for a chronically implantable electrode.

SUMMARY OF THE INVENTION

In accordance with the teachings of the present invention, an implantable electrode is provided which includes a flexible polymeric substrate which has a metallized surface layer. This metallized surface layer forms one or more, depending upon the shape or configuration desired, electrically conductive regions on the surface of the polymeric substrate. The electrically conductive regions are connected via insulated conductors to the cardiac pulse generating system.

In accordance with one preferred embodiment, the flexible polymeric substrate is a silicone rubber tube, and the metallized surface layer is a preselected region on the outer surface of the tube which has been impregnated by a metal such as platinum, effectively minimizing the boundary layer between the dissimilar silicone rubber and metallic materials. If desired, additional depositions of metallic surface coatings can be made on the electrically conductive region. A conductor connected to the proximate terminal is electrically connected to this metallized surface layer, using any conventional technique including, but not limited to, conductive epoxy, interference fitting between metal rings, swaging the conductors to a termination collar in contact with the metallized surface area, design of the conductor and tubing such that the conductor terminates in the metallized surface layer, and the like.

In accordance with another preferred form of the invention, the polymeric substrate forms a planar discharge surface. A predetermined portion of this surface is impregnated with a metal, such as platinum. The impregnated surface layer forms a desired configuration (pattern) on the planar surface, such as a concentric ring, a mesh grid, or a spiral configuration. The metallized surface layer is conductively connected to the leads of the electrode.

Accordingly, it is an object of the present invention to provide an electrode having a metallized outer surface layer formed on an underlying polymeric substrate, whereby electrical signals may be conducted to and from the heart via the metallized surface layer.

It is a further object of the present invention to provide an electrode of the type described above whereby the polymeric substrate together with the metallized outer surface layer form a predetermined shape, including tubular or planar electrode shapes.

It is a yet further object of the present invention to provide an electrode having a predetermined conducting surface layer configuration for conducting electrical signals to and from the heart, which surface layer is formed by the impregnation of metal in a predetermined pattern in a polymeric substrate.

A still further object of the invention is to provide an electrode having a low profile, flexible, biocompatible, and less abrasive exterior surface. The above and further objects and advantages of this invention will better be understood by referring to the following description of illustrative embodiments of the invention, taken in connection with the accompanying drawings.

BRIEF DESCRIPTION OF THE DRAWINGS

FIG. 3 is a cross sectional view illustrating an electrode in accordance with a second embodiment of the invention.

FIG. 4b is a top view of the electrode of FIG. 4a.

DETAILED DESCRIPTION OF THE DRAWINGS

Figure 1:
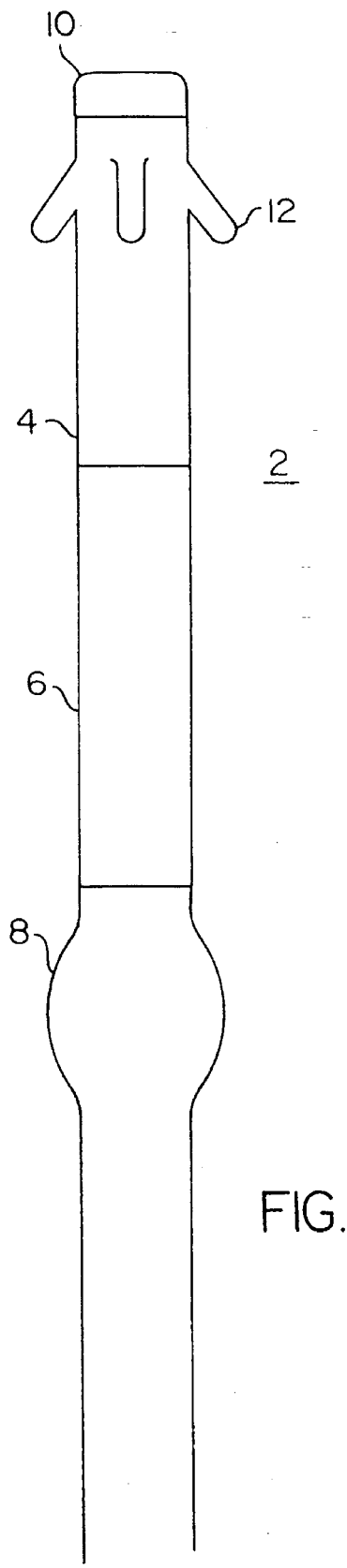
FIG. 1 is a side view of an electrode illustrating a first embodiment of the invention.

Referring first to FIG. 1, an implantable electrode of the first embodiment of the present invention is shown. Electrode 2 is shown as a tubular element having two discharge regions, metallized surface 6 and pacing tip 10. The inner tubing 4 of electrode 2 is formed from a polymer biocompatible for implantation, and preferably is a silicone rubber polymer. Tines 12 are conventional, aiding with the fixation of electrode 2 in the desired location proximate the heart.

Figure 2:
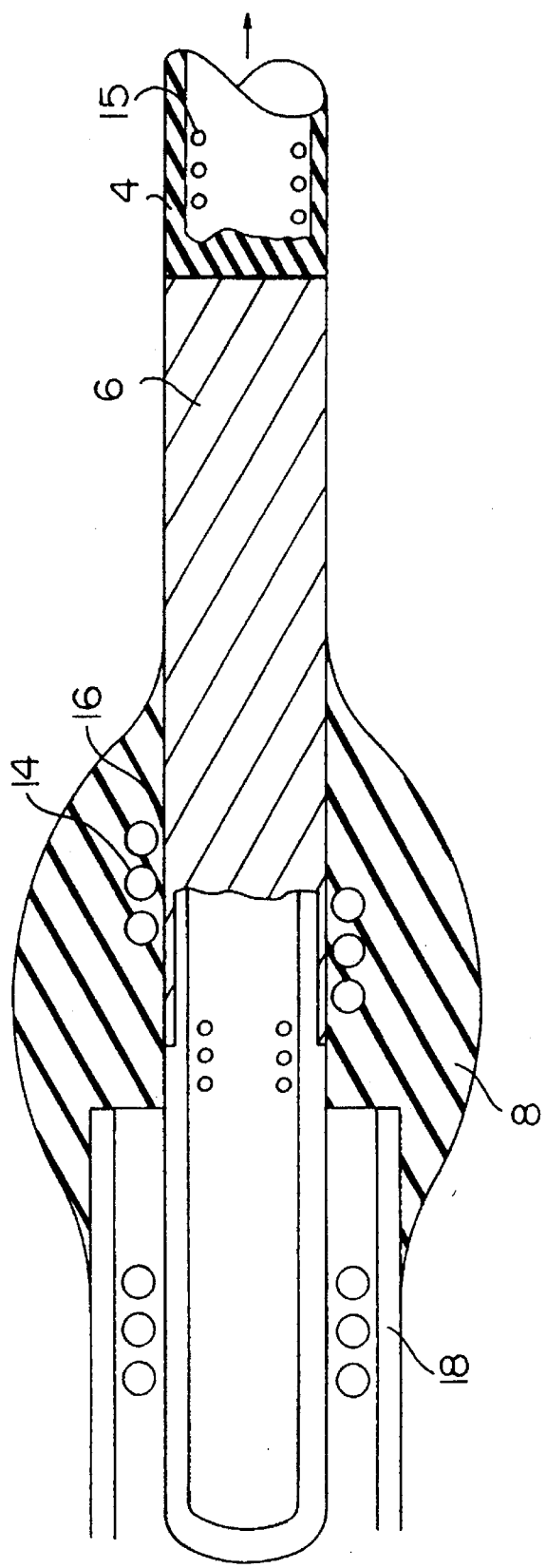
FIG. 2 is a cross sectional view of the electrode of FIG. 1.

Referring to FIG. 2, a cross section of electrode 2 is illustrated. Inner tubing 4 and outer tubing 18 form a coaxial lead, with outer conductor 14 coiling around inner tubing 4 and inner conductor 15 coiling within the interior of inner tubing 4. Metallized surface 6 forms a band around the exterior of inner tubing 4. Outer conductor 14 terminates in conductive contact with metallized surface 6, being secured to metallized surface 6 via conductive epoxy 16. To further secure the connection between outer conductor 14 and metallized surface 6 a high durometer (stiff) strain relief 8 is formed surrounding this connection and the end of outer tubing 18.

The metallized surface 6 is formed by impregnating the desired location(s) on the outer surface of inner tubing 4 with a metal. This impregnation preferably occurs by ion impregnation or ion enhanced metallization (high energy metal impregnation and deposition). Preferably inner tubing 4 is formed from a polymer such as silicone rubber and the metal atoms used to impregnate inner tubing 4 are platinum. A high energy vapor or ion impregnation process impregnates the silicone rubber with platinum atoms, making the metallized surface 6 of the silicone rubber tubing 4 conductive. This metallization "sticking" process also effectively eliminates the boundary conditions that would otherwise exist between these dissimilar materials. By eliminating the boundary conditions, this process also eliminates the high stress areas otherwise found around metal particles that could cause fatigue in high-flexed applications. Further, the metallized surface 6 typically includes one or more additional layers of metal deposited as a metallic film on the previously impregnated surface of the polymer. The previously impregnated metal in the polymer substrate provides an effective adhesion surface for the subsequent metallic coating, and effectively eliminates any discrete boundary or layering between the polymer substrate and the metallized surface. As can be appreciated, this elimination of discrete boundaries or layers provides for neutral stresses at the boundary and greatly improves the flex life of the metallic surface of the electrode 2.

The depth of the conductivity of metallized surface 6 can be determined as function of the energy applied during the impregnation, the ion mask of the metal impregnating the polymer, the focus, and the deposition time of the impregnation process. One skilled in the art may vary these parameters to obtain the desired thickness and conductivity of the metallized surface 6. Further, by altering the impregnation pattern and focus, different configurations of the metallized surface 6 can be formed on the surface of the polymer substrate. By using masks or other fixtures, any one of a number of configurations, including bands, concentric circles, spirals, and cross hatching, can be formed on the electrode surface. This important feature of the invention allows one skilled into the art to selectively tailor conductive configurations on the surface of an electrode to the desired application by varying the design, depth and conductivity of metallized surface 6 during the impregnation process.

Further, by metallizing the outer surface of inner tubing 4, the need for a discrete metallic electrode is obviated and the required surface electrode diameter reduced. This in turn allows the overall diameter of the lead to be reduced. Further, the elimination of discrete metallic surface electrodes also eliminates the surface roughness associated with these discrete elements and reduces the stiffness of the lead at the location of the electrode. Thus, the use of metallized surface 6 in place of earlier types of discrete metallic electrodes allows for a thinner, smoother, and more flexible lead that will be less traumatic to the patient, easier to manipulate, and easier to remove chronically.

In order to maintain a smooth surface on the electrode at the point of connection between outer conductor 14 and metallized surface 6, a molded strain relief 8 is formed over this connection. Mold 8 is preferably a high durometer (stiff) molded strain relief, made of a higher durometer rubber with feathered cross-section.

Turning to FIG. 3, an electrode 22 of a second embodiment of the invention is illustrated. Outer tubing 24 is formed from a polymeric substrate, preferably a silicone rubber, with two metallized surfaces 26, 28 formed on the outer surface of outer tubing 24 via impregnation of a metal in the polymeric substrate, the metal preferably being platinum. Conductors 30–33 are embedded in the outer tubing 24, with conductor 30 being conductively connected to metallized surface 26 and conductor 31 being conductively connected to metallized surface 28. Conductors 32, 33 may be used to connect other conductive surfaces on the distal end of the electrode assembly. Conductors 30–33 are in turn connected to the desired pulse generator system (not shown). Conductors 30, 31 are conductively connected to metallized surfaces 26, 28, and are preferably connected by the proximal placement of the termination of conductors 30, 31 to the outer surface to tubing 24 such that during the metallic impregnation process forming metallized surfaces 26, 28 the impregnating metal penetrates sufficiently to form the desired conductive connection between metallized surfaces 26, 28 and conductors 30, 31.

Conductors 30–33 are embedded in tubing 24 such that the polymeric substrate of tubing 24 insulatively surrounds conductors 30–33. However, in a preferred embodiment further insulation 34–37 surround conductors 30–33, and is embedded in tubing 24 along with conductors 30–33.

Inner tubing 38 surrounds inner conductor 39, and in a preferred embodiment is used to connect the pulse of the generating system to a pacing tip electrode. Thus, in one embodiment of the present invention a lead 22 may incorporate a variety of different electrode configurations, such as one including a pacing tip, a bipolar ring, and two defibrillation electrodes while still allowing for a thin, smooth, and flexible electrode.

While metallized surfaces 26, 28 have been illustrated as rings on the surface of outer tubing 24, one skilled in the art will appreciate that many different configurations of these metallized surfaces may be formed, and many different combinations of electrode surfaces may be placed on a given electrode. It is a particular advantage of the present invention that a variety of electrode surface configurations and combinations of electrode surfaces may be placed on a unitary electrode while still allowing the lead to be constructed as a thin, flexible, and smooth surface electrode.

In one embodiment, metallized surfaces 26, 28 are formed following the manufacture of outer tubing 24. One skilled in the art will appreciate, however, that when outer tubing 24 is formed by an extrusion process metallized surfaces 26, 28 may be formed by high energy metal deposition of the polymer substrate immediately following the extrusion of the substrate into the form of outer tubing 24. An uncured silicone rubber may thus be used, and further, the heat, radiation or the like from the ion implantation process may be used to cure the unpolymerized material, allowing for a unique way in which to bond, affix and fabricate various subassemblies within the catheter or patch.

Figure 4A:
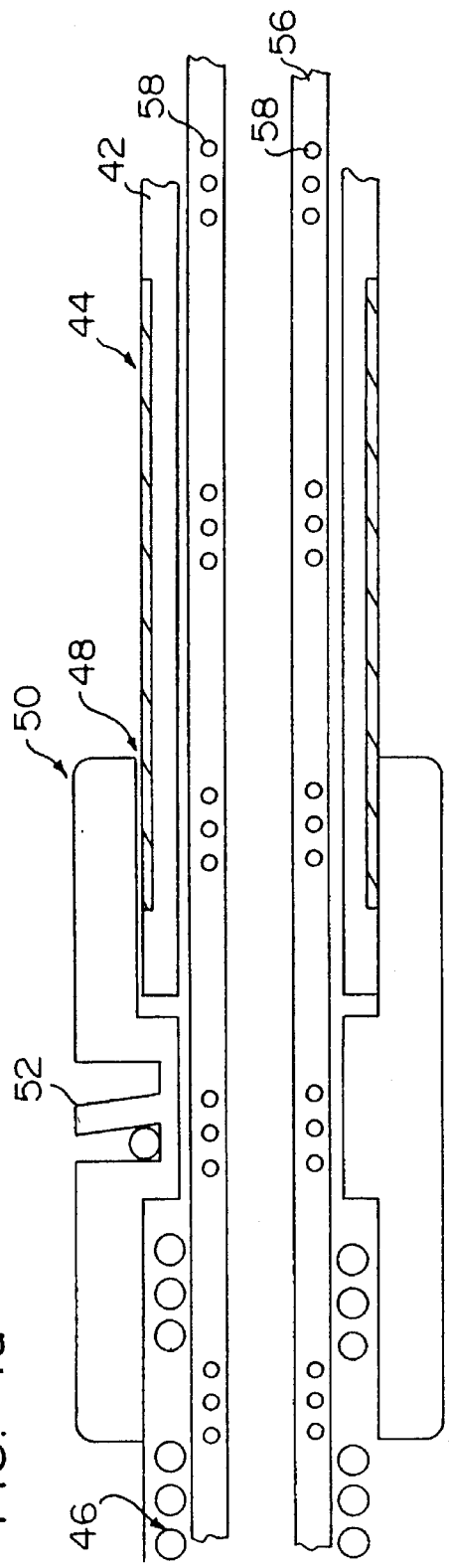
FIG. 4a is a cross sectional view of an electrode illustrating a third embodiment of the invention.
Figure 4B:
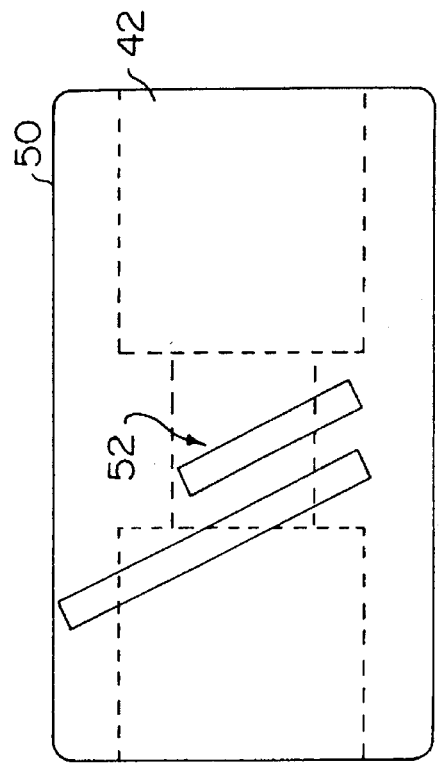

Turning now to FIG. 4a, electrode 40 illustrates an alternate approach towards connecting the metallized surface 44 to an outer conductor 46. In this embodiment outer tubing 42, outer conductor coil 46, inner tubing 56, and inner conductor coil 58 together form a coaxial tubing, similar to the lead 2 illustrated in FIG. 1, such as may be used by for a simple bipolar lead. Unlike lead 2 in FIG. 2, however, conductor coil 46 in lead 40 is connected to metallized surface 44 by a termination ring 50 in this embodiment. Thus, outer conductor coil 46 is connected to the termination ring 50 via a swage termination 52. Termination ring 50 is connected on its surface to metallized surface 44 via a conductive epoxy 48. FIG. 4b further illustrates a top view of such a termination ring assembly.

Figure 5:
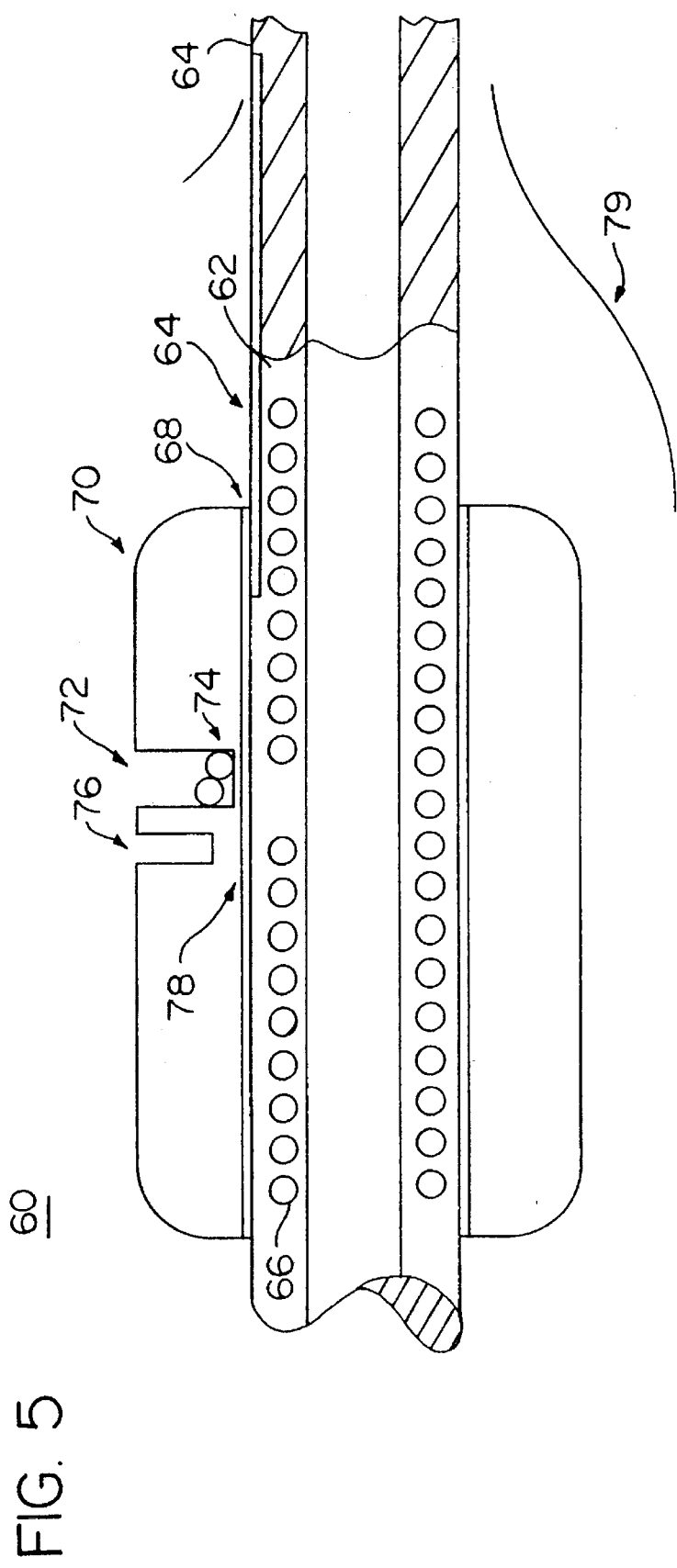
FIG. 5 is a cross sectional view of an electrode in accordance with a fourth embodiment of the invention.

FIG. 5 illustrates an electrode 60 according to a fourth embodiment of the present invention. In this embodiment a plurality of electrical conductors 66 are helically wound at a predetermined pitch within tubing 62. At the desired location a metallized surface 64 is formed by impregnation in tubing 62. Selected conductors 74 are lifted from the tubing structure and connected to termination collar 70, using a method similar to that disclosed in Dahl et al. U.S. Pat. No. 4,559,951. The selected conductors 74 are lifted into slot 72 and swaged or crimped to the termination collar 50 by means of swaging or crimp groove 76. Slot 72 and groove 76 are then back-filled with a medical adhesive 78.

Termination collar 70 is conductively connected to metallized surface 64, preferably by means of a conductive epoxy joint 68. After the connections have been made, the termination collar 50 and a portion of metallized surface 64 are then preferably encapsulated in a strain relief mold 79.

Figure 6:
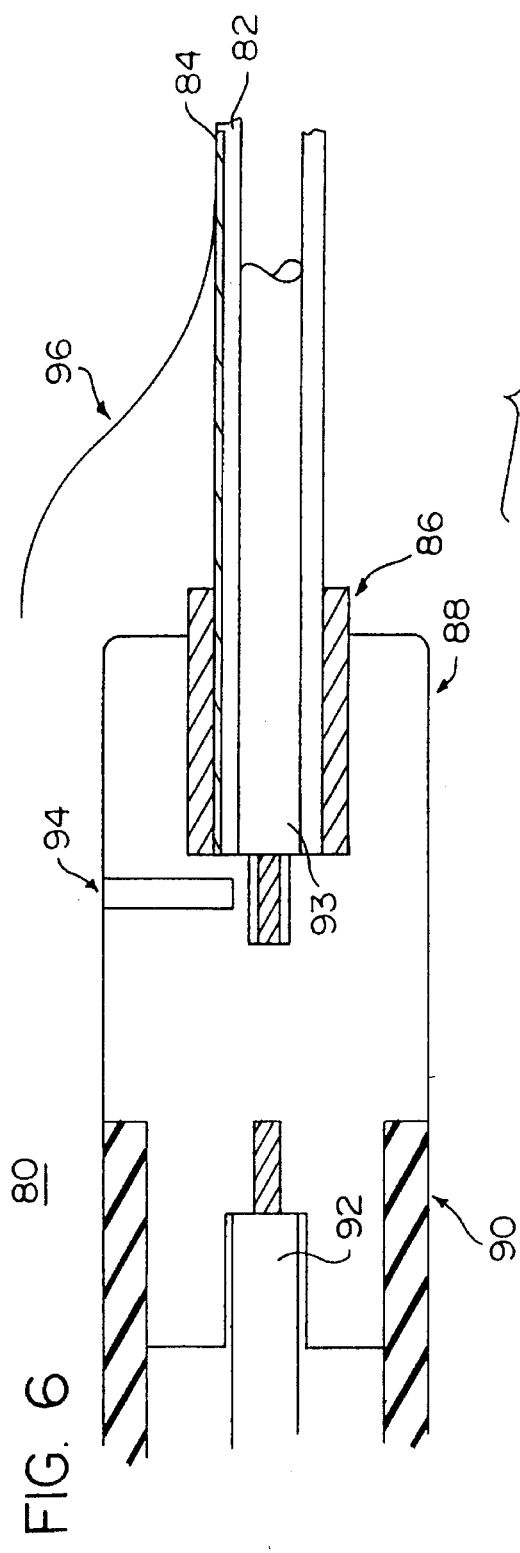
FIG. 6 is a cross sectional view of an electrode illustrating a fifth embodiment of the invention.

FIG. 6 illustrates a fifth embodiment of the present invention for use with a SQA termination for subcutaneous or epicardial electrodes. Polymer tubing 90 and conductor 92 are joined via cylindrical terminal block 88 to tubing 82 and conductor 93. Conductors 92 and 93 are preferably teflon coated DBS, and are conductively connected to terminal block 88, preferably by crimping via an access hole or slot 94. Metallized surface 84 on tubing 82 is connectively connected to termination collar 88 via a fully impregnated metallized tubing 86 that is pressure fitted between metallized surface 84 and terminal block 88. Finally, molded strain relief 96 encapsulates terminal block 88 and impregnated tubing 86 while leaving a pre-determined portion of metallized surface 84 exposed.

The use of a metallized surface 84 in a SQA termination, as illustrated in FIG. 6, minimizes the permanent deformation that is associated with crushed coils used in previous SQA electrodes. Instead, the SQA termination of electrode 80 relies on the compression of a fully impregnated conductive tubing 86 between the SQA terminal block and metallized surface 84 for making the electrical connection. Thus, the chronic durability (fatigue resistance) of these electrodes is improved. Further, the use of strain relief molding 96 has the added benefit of providing a smoother connection and minimizing the potential for loss of electrical continuity due to abrasion on the termination connection.

Figure 7:
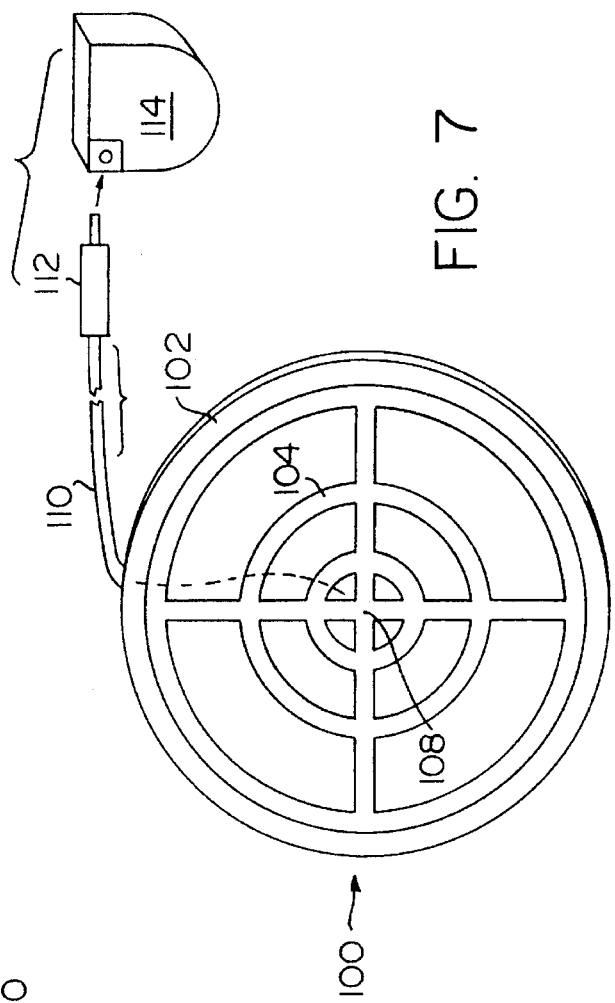
FIG. 7 is a perspective view of an electrode of yet another embodiment of the invention.

FIG. 7 illustrates yet another embodiment of the present invention, as applied to a planar discharge region such as found on patch electrodes. Electrode 100 consists of a polymeric substrate 102 formed into a planar surface configuration. A metallized surface 104 is formed in a desired configuration as a discharge surface in the planar region of polymeric substrate 102. Conductor 108 connects metallized surface 104 to lead 110, which is connected via plug 112 to pulse generating system 114.

As this figure illustrates, it is an advantage of the present invention that an electrical conducting surface of a desired configuration can be formed on a smooth planar surface by metallic impregnation. This is an improvement over prior patch electrode configurations using straight or undulating wires which have poor fatigue resistance; by eliminating such structures the screen fractures associated with such are similarly eliminated, improving electrode fatigue resistance. Further, the smoother surface associated with a metallized surface 104 minimizes localized tissue trauma from the electrode. Moreover, the use of metallized surfaces facilitates chronic patch removal, by inhibiting tissue ingrowth, as well as the development of deployable electrodes using pre-stressed members, without the permanent deformation normally associated with metal parts.

Further, it is a particular advantage of the present invention that both complex and conventional electrode patterns may be readily formed, depending on the desired application. Further, undesirable current distributions can be smoothed in the electrode configuration by altering the conductivity throughout the electrode surface through variations in the impregnation parameters such as energy, ion mask, focus and deposition time. Further, in addition to forming a metallized surface region, it is also possible to form embedded conductors within the polymer substrate by means of a continuous feed extrusion system, where the depth and region of metallization are determined by feeding the extruded polymer between a stimulating electrode on one side and a conductor connecting the stimulating electrode to a terminal pin on the other side while varying the parameters of metal impregnation forming the stimulating electrode.

The invention has been described here in considerable detail in order to provide those skilled in the art with information needed to apply the novel principals disclosed. However, one skilled in the art will appreciate that many different configurations and shapes of the electrode as described herein are possible. Further, it should be understood that the invention can be carried out by other different equipment and processes, and that various modifications, both as to physical details and operating functions, can be effected without departing from the scope of the invention itself. The description herein is intended by way of example only, and is not intended to limit the invention except as set forth in the following claims.

We claim:

1. An electrode adapted for implantation on or about a heart and for connection to a system for monitoring or stimulating cardiac activity, the electrode comprising:

a flexible polymeric substrate formed as a silicone rubber tube having an exposed surface layer;

a region of the exposed surface layer impregnated with a metal to form an electrically conductive surface;

an electrical conductor for electrical connection to the system; and a conductive adhesive joining the conducting surface to the electrical conductor.

2. The electrode of claim 1 further comprising a strain relief encapsulating the electrical conductor.

3. The electrode of claim 1 wherein the metal is platinum.

4. The electrode of claim 1 further comprising a strain relief surrounding the electrical conductor and conductive adhesive, and an outer tubing coaxially disposed around the silicone rubber tube having a distal end terminating within the strain relief, and wherein the conductor is insulatively disposed between the silicone rubber tube and the outer tubing.

5. The electrode of claim 1 wherein the electrode further comprises a termination ring conductively connected to the electrical conductor, and the conductive adhesive joins the termination ring and the electrical conducting surface.

* * * * *

UNITED STATES PATENT AND TRADEMARK OFFICE
CERTIFICATE OF CORRECTION

PATENT NO. : 5,554,178

DATED : September 10, 1996

INVENTOR(S) : Dahl et al.

It is certified that error appears in the above-identified patent and that said Letters Patent is hereby corrected as shown below:

cover page, section 75, please delete "Indianapolis, Ind." and insert --Poway, CA-- therefor.

Signed and Sealed this

Nineteenth Day of August, 1997

*Attest:*

BRUCE LEHMAN

*Attesting Officer*     *Commissioner of Patents and Trademarks*